United States Patent [19]

Miller

[11] 4,416,278
[45] Nov. 22, 1983

[54] BONE PLUG CUTTER

[76] Inventor: Joseph E. Miller, 641 Argyle Ave., Westmont, Quebec, 3C1

[21] Appl. No.: 265,075

[22] Filed: May 18, 1981

Related U.S. Application Data

[63] Continuation of Ser. No. 61,067, Jul. 26, 1979, abandoned.

[51] Int. Cl.³ .................................................. A61B 17/32
[52] U.S. Cl. ........................................ 128/305; 128/92 E; 128/754
[58] Field of Search ................. 128/305, 305.3, 754, 128/753, 751, 92 C, 92 CA, 92 E; 30/316; 83/698, 674, 675, 310

[56] References Cited

U.S. PATENT DOCUMENTS

| 43,909 | 8/1864 | Hair | 128/313 |
|---|---|---|---|
| 218,478 | 8/1879 | Blodgett et al. | 83/633 |
| 367,897 | 8/1887 | Doud | 100/293 |
| 475,559 | 5/1892 | Heydenreich | 408/119 |
| 2,710,000 | 7/1955 | Cromer et al. | 128/754 |
| 3,335,627 | 8/1967 | Smelts | 83/698 X |
| 3,468,312 | 9/1969 | Kuntscher | 128/317 |
| 3,512,519 | 5/1970 | Hall | 128/305 X |
| 3,515,128 | 6/1970 | McEvoy | 128/305 X |
| 3,585,985 | 6/1971 | Gould | 128/751 |
| 3,587,560 | 6/1971 | Glassman | 128/310 X |
| 3,642,002 | 2/1972 | Otterstrom | 128/317 |
| 3,701,352 | 10/1972 | Bosworth | 128/305 |
| 3,752,161 | 8/1971 | Bent | 128/312 |
| 3,835,860 | 9/1974 | Garretson | 128/310 |
| 3,850,158 | 11/1974 | Elias et al. | 128/310 X |
| 3,857,389 | 12/1974 | Amstutz | 128/92 EC |
| 3,913,566 | 10/1975 | Lacey | 128/310 X |
| 3,949,747 | 4/1976 | Hevesy | 128/754 |
| 3,989,033 | 11/1976 | Halpern et al. | 128/305 X |
| 4,092,005 | 5/1978 | Benroth | 241/168 |
| 4,124,026 | 11/1978 | Berner et al. | 128/303 R |

Primary Examiner—Michael H. Thaler
Attorney, Agent, or Firm—Sherman & Shalloway

[57] ABSTRACT

An apparatus for cutting a bone plug from a portion of bone. A base vertically supports a block. An arm has one end hinged to the block and carries a handle at the other end thereof. A sleeve is connected to the block and extends below the handle. A plunger is disposed within the sleeve and connected to the arm via a roller pin and roller which are disposed in an arcuate slot in the handle. The lower end of the plunger carries a die for cutting the bone plug. The handle is raised, pivoting the arm and causing the plunger to move within the sleeve and away from the base. A portion of bone from which the bone plug is to be cut is placed between the die carried on the plunger and the base. As the handle is moved downward toward the base, the lever action forces the plunger to close onto the portion of bone causes the die to penetrate the portion of bone resulting in a bone plug cutting. A plurality of stems may be located on the sleeve or provided on a separate flat plate for storing extra dies. In addition, a stem is located on the base to aid in removing the bone plug from the die.

5 Claims, 6 Drawing Figures

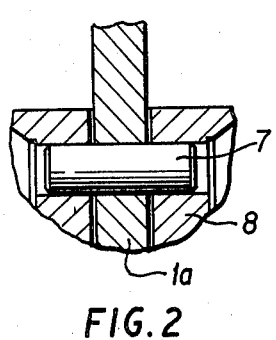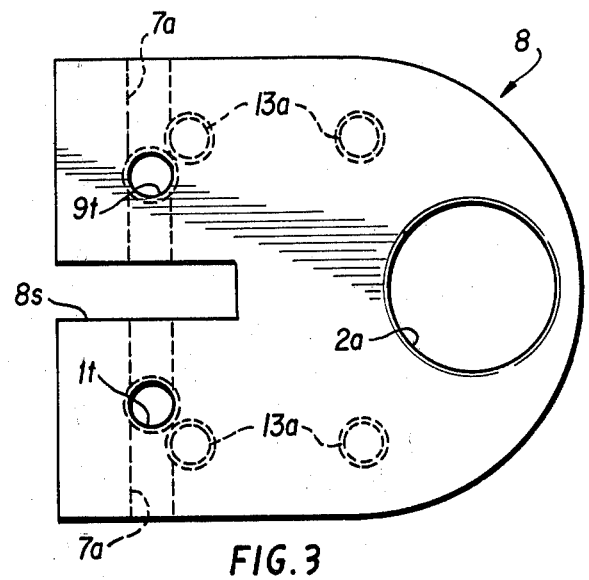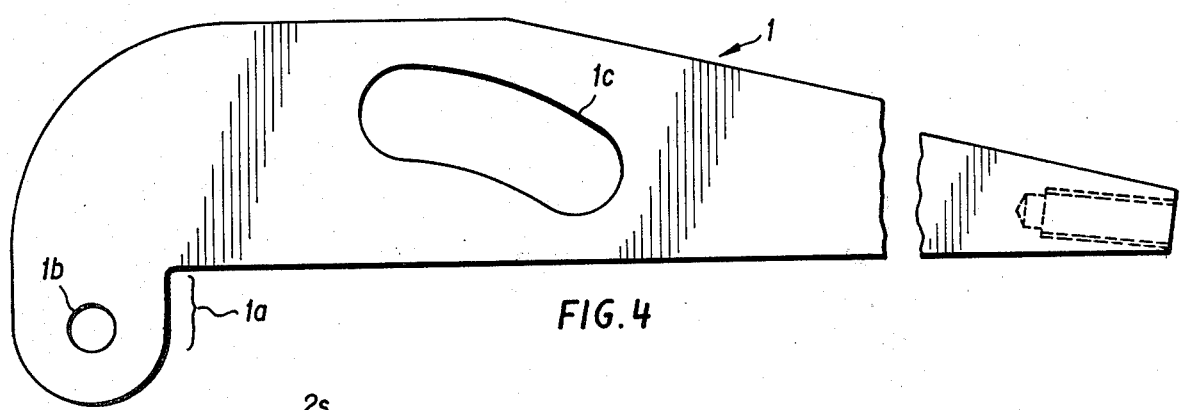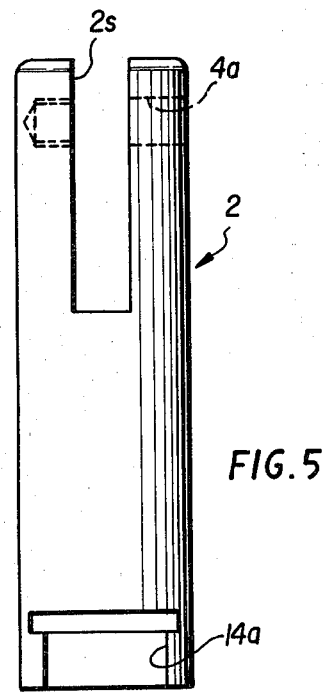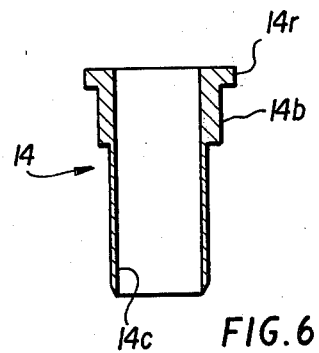

BONE PLUG CUTTER

This is a continuation, of application Ser. No. 061,067, filed July 26, 1979, now abandoned.

BACKGROUND OF THE INVENTION

1. Field of the Invention

The invention generally relates to an apparatus for cutting a bone plug and, more particularly, relates to a structure in the form of a Class 2 lever for cutting a bone plug from a portion of bone, the bone plug to be used in implanting a prosthesis.

2. Description of the Prior Art

Many types of structure are known in the prior art for accomplishing the bone cutting function. For example, U.S. Pat. No. 3,835,860 issued to Garretson describes a surgical bone punch in the form of a Class 1 lever for punching holes in bone or other substantially solid matter such as cartilaginious tissue. U.S. Pat. No. 3,850,158 issued to Elias, et al., discloses a bone biopsy instrument comprising an abturator in the form of a rod-like member having an enlarged head at one end and a wedged shaped cutting and scraper blade at its opposite distal end slideably fitted into a tubular sheet. Other types of biopsy instruments are disclosed in U.S. Pat. Nos. 3,512,519; 3,515,128; 3,587,560; 3,913,566; and 3,989,033.

SUMMARY OF THE INVENTION

It is an object of this invention to provide a bone plug cutter of the class 2 lever category for cutting a bone plug from a portion of bone, the bone plug to be used in the implantation process of a prosthesis.

It is a further object of this invention to describe a manual structure which provides for a high mechanical advantage allowing a single individual to easily and conveniently cut a bone plug from a portion of bone.

It is further object of this invention to describe a structure for a bone plug cutter which has very few parts which are easily assembled and disassembled, facilitating autoclaving of the structure.

It is yet another object of this invention to describe a bone plug cutter which easily and conveniently can hold a selected number of different size dies so that bone plugs of different size may easily and conveniently be cut.

The bone plug cutter includes a first means for retaining the portion of bone in a given position. Preferrably, the first means is comprised of a base, a vertical support having a first end connected to the base and a second end vertically projecting from the base. A second means is provided for cutting the bone plug from the portion of bone and includes an interchangeable die support. A third means is provided for forcing the second means for cutting the bone plug into the portion of bone as the base holds the portion of bone. Preferably, the third means is in the form of a longitudinal member having a first end hinged to the second end of the vertical support.

A second end of the longitudinal member forms the handle for the bone plug cutter and the central portion between the first and second ends has an arcuate opening therein. In particular, the die support is connected to the longitudinal member via a roller pin and roller disposed within the arcuate opening. Downward pressure on the handle end of the longitudinal member causes the die support to move toward the base. The portion of bone is, therefore, sandwiched between the die support and the base so that the bone plug may be cut from the portion of bone. Stop means are provided for stopping the movement of the guide support and die toward the base, after the bone plug is cut, to prevent damage to the die. A dish-shaped opening is provided within the base and below the die so that the die does not come into contact with the base.

BRIEF DESCRIPTION OF THE DRAWINGS

These features and objects of the invention will become apparent to one skilled in the art by referring to the specification and accompanying drawing in which:

FIG. 2 is a partial sectional view taken along lines 2—2 of FIG. 1 showing the hinge structure of the bone plug cutter according to the invention;

FIG. 3 is a top view of the sleeve which forms the guide for the die support of the bone plug cutter according to the invention;

FIG. 4 is a side view of the longitudinal member in the form of an arm;

FIG. 5 is a rear view of the die support portion in the form of a plunger of the bone plug cutter; and FIG. 6 is a front view of a die for use with the bone plug cutter of the invention.

DETAILED DESCRIPTION OF THE INVENTION

Figure 1:
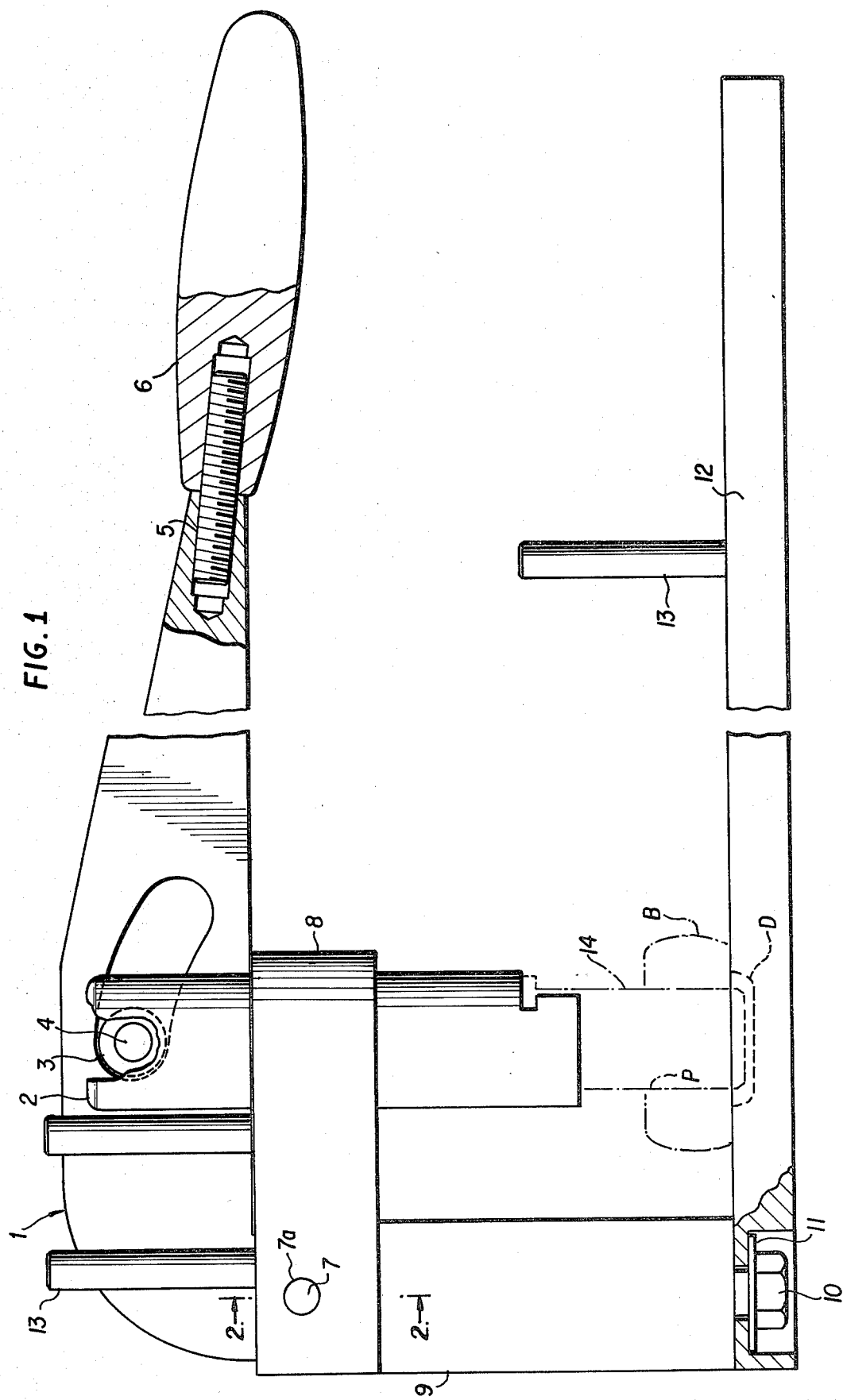
FIG. 1 is a side view of the bone plug cutter apparatus.

A basic and critical feature of the invention is that it is constructed in the form of a class 2 lever. In particular, the resisting force, which is the force created between the portion of bone to be cut and the die to cut the bone plug, is located between the fulcrum or hinge point of the device and the handle or point of force application of the device. This aspect of the invention can best be appreciated by referring to FIG. 1, a side view of the preferred embodiment. Base 12 is attached to a vertical support in the form of block 9 by a hexhead bolt 10 and washer 11 which engages the block 9. The block 9 horizontally supports a vertical member in the form of sleeve 8. The intersection of block 9 and sleeve 8 form the fulcrum point of the structure with arm pin 7 functioning as the hinge point for interconnecting arm 1 with sleeve 8. In particular, two hexhead bolts 10 extend the length of block 9 and engage the threaded openings 9t to firmly hold the sleeve 8, block 9 and base 12 interconnected so that the sleeve 8 is parallel to the base 12. The upper portion of sleeve 8 forms a stop for stopping the downward movement of arm 1 and to stop the downward movement of the die 14 to a point just below the surface of base 12.

As shown in FIG. 4, arm 1 includes an extension 1a with an opening 1b therein. Sleeve 8 is provided slot 8s for receiving the extension 1a so that the opening 1b is in registry with aperture 7a in sleeve 8. Arm pin 7 is placed within the registered apertures to hingedly interconnect the arm 1 and sleeve 8. As shown in FIG. 1, in the closed position the arm 1 is generally parallel to and has the same length as base 12.

Stud 5 interconnects the tapered end of arm 1 with a handle 6 to further lengthen the mechanical advantage provided by the arm 1 and to provide a convenient grasping structure for moving the handle in a clockwise or counterclockwise direction.

The means for cutting the bone plug from the portion of bone is a die support which is hinged to the central portion of the arm 1 and vertically supported by the sleeve 8. In particular, plunger 2 of generally cylindrical shape is located with aperture 2a of sleeve 8. As can be appreciated by referring to FIG. 5, the upper portion of sleeve 2 includes a slot 2s therein for receiving the arm 1. Arcuate opening 1c is provided within the arm 1 so that, when arm 1 is engaged by the slot 2s of plunger 2, opening 4a is in registry with arcuate opening 1c. A roller 3 is disposed within arcuate opening 1c and a roller pin 4 is located within the roller pin opening 4a and the roller 3. The lower end of plunger 2 is provided with an aperture 14a for receiving a die 14, shown in FIG. 6. Preferably, the die has a base 14b with ridge 14r thereon for insertion into the aperture 14a. However, it is contemplated that any convenient arrangement for mating the die 14 and the plunger 2 may be employed. For example, the die may be threaded into the plunger or a pin may be provided to hold a die in place in the plunger. In order to prevent damage to the die 14, a dish-shaped opening D is provided within the base 12 and below the die 14 so that the die itself does not come into contact with the metal base.

It is contemplated that the bone plug cutter of the invention would include 4 or 5 dies of various size to facilitate cutting bone plugs of different size. In order to store the dies, stems 13 may be located within stem openings 13a in the sleeve 8 so that the upwardly projecting stems may support the dies thereon. Alternatively, the stems may be located on a separate plate (not shown) for convenient storage. It is further contemplated that a stem 13 may be located within the base 12 to facilitate removal of a bone plug which is within a die. Specifically, the die may be removed from the plunger and pressed onto the stem 13 located on the base 12 so that the bone plug within the die would be pushed out from the bore 14c within the die 14.

MODE OF OPERATION OF THE INVENTION

It is especially contemplated that the bone plug cutter may be used to cut a bone plug which improves the retention of the bone cement mass and thereby facilitates the implantation of a prosthesis during total hip arthroplasty. The common complication during total hip arthroplasty has been loosening of the femoral component, and occasionally, fracture of the component itself. Plugging the femoral canal about six inches distal of the calcar not only prevents the extension of the cement beyond the point where it is useful, but also creates a closed space which facilitates complete filling of the femoral canal. The subsequent introduction of the femoral component into this closed space introduces a rise in pressure in the cement inducing it to penetrate into the interstices of the endosteal bone. The presence of the plug reduces the amount of blood entering the proximal femoral canal from distal medullary vessels. The presence of the plug also diminishes the tendency for fat and air to be forced into the venous circulation at the time when the prosthesis is inserted. The primary purpose of the plug is to create a closed base which can be filled completely and efficiently with acrylic cement, and which facilitates a rise in pressure in the acrylic during stem insertion to induce an optimum interface between cement and bone. The plug prevents movement of the cement mass while under pressure in the distal end of the canal where such movement is not wanted. The plug further allows pressure to be created because of the filling of the canal and subsequent to the pressurization with the cement gun. The plug also allows a significant pressure when the stem of the implant is inserted into the cement.

Using a plug of bone which can be cut by the disclosed invention allows the material introduced into the femoral canal to be of biological rather than foreign type matter such as an acrylic plug or polyethylene plastic-type plug. Further, the invention allows a plug to be cut of any size and which conforms and compacts in the irregularly shaped canal. Most important, a bone plug cut by the disclosed device assures that the canal will be plugged, something which cannot be guaranteed when liquid acrylic is introduced beyond that point where it can be visually inspected.

After the patient is anesthetized, prepped and draped for total hip arthroplasty and the hip joint has been exposed and located, the head and neck are resected as one piece, with a saw cut at the base of the neck. To facilitate the preparation of a bone plug, an extra saw cut is placed at the junction between the head and neck so that the femoral neck is available as a separate piece of bone. The femoral canal is prepared in the usual fashion using a rasp and reamers.

The diameter of the canal six inches distal to the calcar is estimated by preoperative x-rays or physical measurement.

The disclosed bone plug cutter is then used to fashion a bone plug from the resected femoral neck. A die of the proper diameter is selected and located within the end of the plunger 2 as shown in phantom in FIG. 1. The arm 1 is then raised by drawing the plunger 2 away from the base 12 creating an opening therebetween within which the resected femoral neck may be located. Alternatively, the bone from the femoral head may be placed under the cutting head. The handle 6 is then pushed down firmly forcing the die 14 through the bone B and cutting a plug P therefrom. Stop means are provided to limit the downward movement of the handle and to stop the downward movement of the die to a point just below the surface of the base. In order to prevent damage to the die, a dish shaped opening D is provided within the base 12 and below the die 14 so that the die itself does not come in contact with the metal base.

The die 14 should be chosen so that it will produce a plug slightly larger than the femoral canal. The size of the femoral canal may be determined by any convenient method. For example, an x-ray study of the estimated diameter of the intermedullary canal may be used. Alternatively, the size of the rasp or reamer used can form the basis of determining the size of the femoral canal. Also, sounding plugs may be used to determine the canal size. The die 14 with the impaled bone plug P therein is removed and stem 13 located on base 12 is employed to push the plug out of the die 14. Occasionally, difficulty can be encountered in removing the impaled bone from around the die 14, but this can be resolved by using a bone cutting forceps.

Preferably, the dies 14 are structured to be one and one half inches in length and the bone to be cut must be not thicker than this. The bone plug is then introduced into the canal. When the preparation of the canal is complete, the bone plug is inserted into the canal with gentle tapping of a mallet and inserting instrument.

All surgical debris, bone cuttings and blood clots are then cleaned from the femoral canal in some suitable fashion. The canal is then filled from bottom to top with a low viscosity cement, and subsequently pressurized with a gun to improved penetration into the bone.

When the canal has been filled, the femoral component is inserted with an even, steady motion making certain to avoid a varus position. Once the stem has been inserted, its position should not be changed as it will have an adverse affect on the cement-stem interface. The femoral canal, full of cement and plugged, functions as a closed space and the mere act of introducing this tapered stem produces a hydrostatic pressure which tends to force the cement outwards to interlock with the irregularities of the indosteal surface of the bone. By using this technique, the plug can be found, on post operative x-ray, to be place in a position such that there is about one inch of acrylic cement distal to the tip of the prosthesis.

It is contemplated that each of the parts of the bone plug cutter as described herein may be of metal or other rigid material which will easily survive autoclaving. However, it is also contemplated that the bone plug cutter according to the invention may be developed of inexpensive rigid plastics to form a disposable type of cutting system not requiring autoclaving or reuse. Various changes may be made in the details of the invention, as disclosed, without sacrificing the advantages thereof or departing from the scope of the appended claims. Furthermore, although the present invention has been disclosed and discussed with particular regard to its exceptional advantages in terms of a bone plug cutter, it may be understood that the invention may be employed in several industrial applications wherein a manual plug cutter is required.

What is claimed is:

1. A bone plug cutter for cutting a bone plug from a portion of the bone comprising:
   (a) a base for retaining a portion of the bone in a given position;
   (b) a vertical support having first and second ends, the first end of the support connected to the base;
   (c) a longitudinal member having a first end, a second end and a central portion interconnecting the first and second ends of the longitudinal member, the first end of the longitudinal member is hinged to the second end of the vertical support, a die support is hinged to and supported by the central portion of the longitudinal member and has an aperture therein for receiving an interchangeable die, said die support containing a die for cutting the bone plug, whereby downward pressure on the second end causes the die support and die to move toward the base so that the bone plug may be cut from the portion of the bone located between the base and the die;
   (d) stop means for stopping the movement of the second end of the longitudinal member and of the die toward the base after the bone plug is cut, to prevent damage to the die; and
   (e) a guide connected to said vertical support, said guide having an aperture therein for receiving the die support and guiding the die support in a substantially vertical direction as the longitudinal member is rotated about the vertical support whereby said guide provides said stop means; and
   (f) wherein a hollow dish-shaped opening is provided within the base and below the die so that when the longitudinal member is stopped by said stop means, the cutting end of the die rests within said opening and does not come into contact with the base.

2. The bone plug cutter of claim 1, wherein the second end of the longitudinal member has a handle attached thereto and the central portion of the longitudinal member has an arcuate opening therein; and wherein said die support has an opening, and a pin located in the opening in the die support and in the arcuate opening.

3. The bone plug cutter of claim 1 which further comprises a stem located on said base said stem providing means to push a bone plug out of said die.

4. The bone plug cutter of claim 1 wherein said die is capable of cutting bone plugs from bone portions up to about 1½ inches in thickness by the application of downward pressure on the second end of the longitudinal member.

5. The bone plug cutter of claim 1 wherein the end of the die support which is hinged to and supported by the arcuate opening has a slot for receiving the central portion of the longitudinal member including the arcuate opening and a roller pin opening in the die support passing perpendicularly through the slot, said roller pin opening being in registry with the arcuate opening, a roller disposed within said arcuate opening and said slot and a roller pin located within the roller pin opening and the roller and disposed within the arcuate opening for supporting said die support.

* * * * *